(12) United States Patent
Saito (10) Patent No.: US 9,750,452 B1
(45) Date of Patent: Sep. 5, 2017

(54) TECHNIQUE FOR DETERMINING SLEEPING STATE OF USER

(71) Applicant: KOEI TECMO GAMES CO., LTD., Kanagawa (JP)

(72) Inventor: Takashi Saito, Kanagawa (JP)

(73) Assignee: KOEI TECMO GAMES CO., LTD., Kanagawa (JP)

(*) Notice: Subject to any disclaimer, the term of this patent is extended or adjusted under 35 U.S.C. 154(b) by 0 days.

(21) Appl. No.: 15/409,804

(22) Filed: Jan. 19, 2017

(30) Foreign Application Priority Data

Feb. 17, 2016 (JP) .................................. 2016-028026

(51) Int. Cl.
*G08B 23/00* (2006.01)
*A61B 5/00* (2006.01)
*A61B 5/11* (2006.01)

(52) U.S. Cl.
CPC .......... *A61B 5/4812* (2013.01); *A61B 5/1114* (2013.01); *A61B 5/4836* (2013.01); *A61B 5/7278* (2013.01); *A61B 5/742* (2013.01); *A61B 5/746* (2013.01)

(58) Field of Classification Search
CPC combination set(s) only.
See application file for complete search history.

(56) References Cited

U.S. PATENT DOCUMENTS

| 2016/0062125 A1* | 3/2016 | Baek .................. G02B 27/0176 361/679.01 |
| 2016/0162012 A1* | 6/2016 | Chang ..................... G06F 3/011 345/211 |

FOREIGN PATENT DOCUMENTS

| JP | H11-249064 | 9/1999 |
| JP | 2010-187132 | 8/2010 |

\* cited by examiner

*Primary Examiner* — Travis Hunnings
(74) *Attorney, Agent, or Firm* — IPUSA, PLLC (57) ABSTRACT

A non-transitory computer-readable recording medium having recorded thereon a program that causes a computer to execute a method to display an image of a predetermined process on a body-mounted display device worn by a user, the method includes tracking a head or the like of the user, and calculating the position and the direction of the head or the like; displaying the image of the predetermined process in a virtual space of the display device; determining that the user is in the sleeping state when a candidate state, in which at least either of the calculated position and direction of the head or the like of the user is shifted by greater than or equal to a predetermined set amount, continues for greater than or equal to a predetermined set period; and performing a predetermined sleeping countermeasure process when the user is determined to be in the sleeping state.

6 Claims, 11 Drawing Sheets

TECHNIQUE FOR DETERMINING SLEEPING STATE OF USER

CROSS-REFERENCE TO RELATED APPLICATION

The present application is based on and claims the benefit of priority of Japanese Priority Application No. 2016-028026 filed on Feb. 17, 2016, the entire contents of which are hereby incorporated by reference.

BACKGROUND OF THE INVENTION

1. Field of the Invention

The present invention relates to a technique for determining a sleeping state of a user.

2. Description of the Related Art

Users play games by wearing a body-mounted display device such as a head mounted display (hereinafter, referred to as a "HMD") connected to a game device, and operating a controller or the like while seeing a screen displayed on the HMD.

For a normal stationary type display connected to a game device, a user can see objects outside a screen of the display. Thus, sometimes, the user cannot concentrate on the screen of the display, or the user cannot be immersed in the game. On the other hand, if the user wears the HMD, the user cannot see objects except a screen image displayed on the HMD. Thus, the user can be immersed in a screen image world, and the user can enjoy the game more.

However, if the game progresses while the user who wears the HMD falls asleep, a disadvantageous situation may occur in the game, or data of the situation of the game before the user falls asleep cannot be saved even though the user hopes to have the data stored. As a result, when the user wakes up, an unintended (undesired) situation of the game may occur.

Thus, a technique is known in which whether a user is in a sleeping state is determined based on whether the user closes his/her eyes, and a predetermined process is performed based on the determined result (see Patent Document 1 and Patent Document 2, for example). For example, Patent Document 1 describes detecting whether a user is in a sleeping state from open-close information of eyes, and displaying images, that were displayed from the time when the sleeping state is detected to the time when the end of the sleeping state is detected, again when the end of the sleeping state is detected. Patent Document 2 describes determining whether a viewer is in a sleeping state or in a gazing state based on whether the viewer closes his/her eyes by irradiating invisible light beam on the eyes of the viewer. Then, when it is determined to be the sleeping state, an alarm is displayed or the like and power is switched off.

However, sometimes, a user may close his/her eyes for a while when the user has tired eyes or the like. Thus, whether the user is in the sleeping state may be wrongly determined if it is determined based on just by tracking the eyes of the user.

PATENT DOCUMENTS

[Patent Document 1] Japanese Patent No. 5,212,155
[Patent Document 2] Japanese Laid-open Patent Publication No. 11-249064

SUMMARY OF THE INVENTION

The present invention is made in light of the above problems, and provides a technique to accurately determine a sleeping state of a user who wears a body-mounted display device, by using a virtual reality technique.

According to an embodiment, there is provided non-transitory computer-readable recording medium having recorded thereon a data processing program that causes a computer to execute a method to display an image of a predetermined process on a body-mounted display device worn by a user, the method including tracking a head, a face or a neck of the user, and calculating the position and the direction of the head, the face or the neck of the user; displaying the image of the predetermined process in a virtual space of the display device such that a position and a direction of the predetermined image corresponds to the calculated position and direction of the head, the face or the neck of the user; determining that the user is in the sleeping state when a candidate state, in which at least either of the calculated position and direction of the head, the face or the neck of the user is shifted by greater than or equal to a predetermined set amount, continues for greater than or equal to a predetermined set period; and performing a predetermined sleeping countermeasure process when it is determined that the user is in the sleeping state.

BRIEF DESCRIPTION OF THE DRAWINGS

Other objects, features and advantages of the present invention will become more apparent from the following detailed description when read in conjunction with the accompanying drawings.

DETAILED DESCRIPTION OF THE PREFERRED EMBODIMENTS

The invention will be described herein with reference to illustrative embodiments. Those skilled in the art will recognize that many alternative embodiments can be accomplished using the teachings of the present invention and that the invention is not limited to the embodiments illustrated for explanatory purposes.

It is to be noted that, in the explanation of the drawings, the same components are given the same reference numerals, and explanations are not repeated.

Here, a virtual reality technique is known. In the virtual reality technique, a coordinate system of a virtual space displayed on a Head Mounted Display (hereinafter, referred to as a "HMD") is corresponded to a coordinate system of a real space of a user who wears the HMD by one to one. Then, the virtual space is displayed on the HMD such that a position or an attitude of a character in the virtual space of the HMD follow a position or an attitude of a head or a face of the user. According to this technique, a character displayed on the HMD can be moved such that the position or the like of the character matches the position or the like of a user itself by tracking the position or the direction of the head or the like of the user who wears the HMD. The following embodiments are performed by using such a virtual reality technique.

(Overall Structure of Data Processing System)

First, an example of an overall structure of a data processing system of the embodiment is described with reference to FIG. 1.

The data processing system of the embodiment includes a HMD 10 and a data processing apparatus 20. In the data processing system of the embodiment, the data processing apparatus 20 performs a predetermined process such as a game process of a predetermined game. Then, images of the predetermined game or the like performed by the data processing apparatus 20 are displayed on the HMD 10. A user U wears the HMD 10 connected to the data processing apparatus 20 on her head, and plays the game by operating a controller 40 while seeing the images displayed on the HMD 10. The user U, using the controller 40, starts and finishes the game, selects items, operates a player character PC in the game. Here, the predetermined process performed by the data processing apparatus 20 is not limited to the game process, and may be a process of playing back screen images of a program or a movie, or the like.

Figure 1:
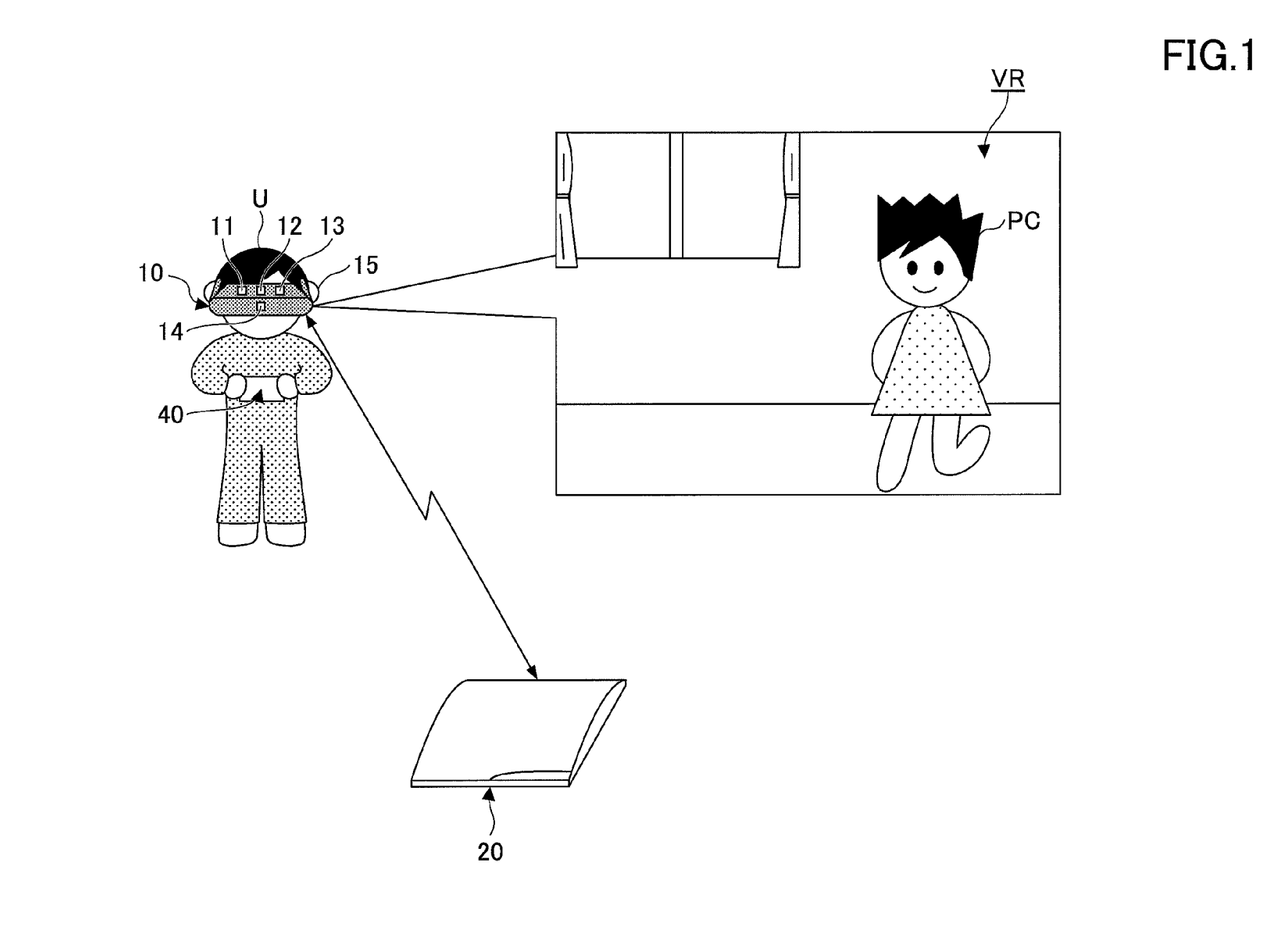
FIG. 1 is a view illustrating an example of an overall structure of a data processing system of an embodiment.

When the user U wears the HMD 10, the user U only sees a screen image that is displayed on the HMD 10 as illustrated in FIG. 1, for example, and the user U cannot see other things. Thus, the user U can be immersed into a screen image world, and enjoy the game more.

An infrared irradiator 11, a color image sensor 12, a six-axis sensor 13, a communication module 14 and a processor 15 are internally or externally provided at the HMD 10.

The infrared irradiator 11 irradiates infrared ray (IR) to a user U side. The color image sensor 12 obtains (photographs) an infrared reflection image from an object such as a head or a face of the user from the user U side. The processor 15 analyzes the infrared reflection image and performs an image recognition process on the object. For example, the processor 15 analyzes the infrared reflection image of the head or the face of the user U, and performs an image recognition process of the head or the face of the user U. Although the color image sensor 12 that uses infrared ray is used, instead of this, or in addition to this, a camera may be used.

Parts of a body of the user U such as the head or the face are recognized by the image recognition on the infrared reflection image obtained by the color image sensor 12. Then, a position of the head, the face, or the neck of the user U in the infrared reflection image is determined. With this, the position of the HMD 10 can be specified based on the position of the head or the like of the user U in a real space. Whether the user U opens or closes her eyes may be determined by tracking the eyes of the user U based on the image of the eyes of the user obtained by the color image sensor 12 or the camera.

The six-axis sensor 13 is a previously known sensor for tracking (motion trace) to detect the motion of the color image sensor 12 in three axis directions including an optical axis direction, a left-right direction, and an up-down direction, or the rotation of the color image sensor 12 around each of the three axes. For example, the six-axis sensor 13 detects acceleration in the three axis directions and angular speed around each of the three axes. Alternatively, the six-axis sensor 13 may detect acceleration in the three axis directions and an earth magnetism direction of north, south, east and west. The data processing apparatus 20 calculates the motion of the user U in the real space from a detected result by the six-axis sensor 13. The data processing apparatus 20 controls a virtual camera such that a position and a direction of the head, the face or the like of the user U in the tracking real space match a position and an attitude of the player character PC in an image obtained by the virtual camera and displayed by the HMD 10. With this, a game image can be displayed in which the position and direction in the virtual space of the HMD 10 correspond to the position and direction of the head or the like of the user U.

The communication module 14 performs a radio communication with the data processing apparatus 20 that performs the predetermined process such as the game process. The data processing apparatus 20 may be connected to a server via a network such as INTERNET or LAN (Local Area Network), for example. In such a case, the server may provide on-line application such as a game to the data processing apparatus 20 in which a plurality of the users U can participate via the network.

In the data processing system of the embodiment, the user U may play the game based on sensor values detected by the above described sensors, without using the controller 40. In such a case, the data processing system may not include the controller 40.

The HMD 10 is an example of the body-mounted display device. As another example of the body-mounted display device, a display device of an eyeglasses type, a goggle type or a helmet (hard hat) type capable of being worn by a user at the user's head or face such as a FMD (Face Mounted Display), for example, may be used.

The data processing apparatus 20 performs a predetermined process such as playing (displaying) a game or a movie or the like, and controls display of images regarding the process performed at the body-mounted display device. The data processing apparatus 20 may be, not limited to a game device, a PC (Personal Computer), a smartphone, a video camera, a digital camera, a PDA (Personal Digital Assistants), a mobile phone, a portable music player, a portable screen image processing apparatus or the like, for example. The predetermined process may be, not limited to a playing process of a game or a movie, any processes in which images are displayed.

Further, although the HMD 10 and the data processing apparatus 20 are separately configured in the data processing system of the embodiment, this is not limited so. The data processing apparatus 20 of the embodiment may be integrally configured with the HMD 10. In such a case, the data processing apparatus 20 is configured as the HMD 10 that displays an image or the like of a game being progressed.

(Hardware Structure of Data Processing Apparatus)

Figure 2:
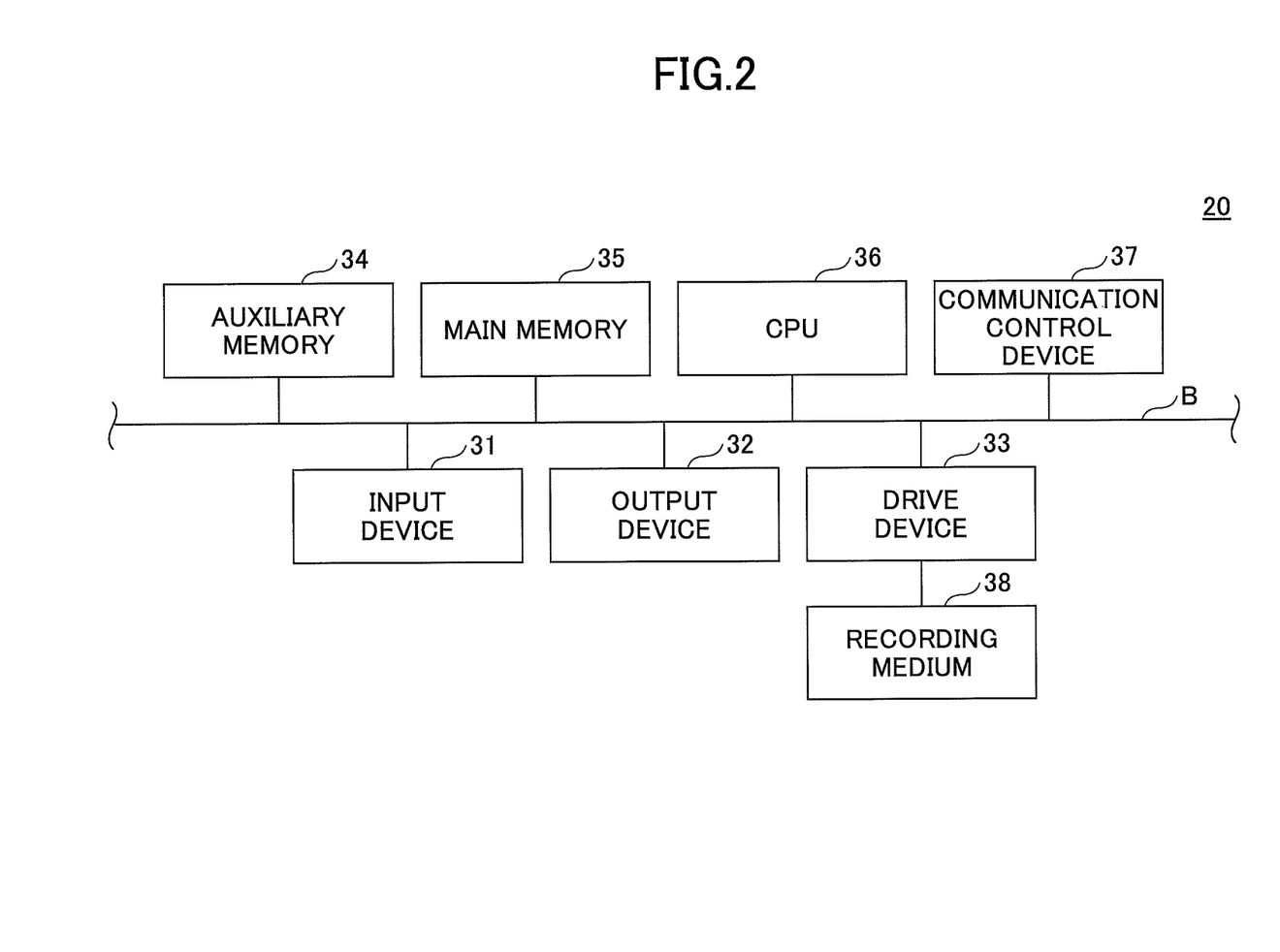
FIG. 2 is a view illustrating an example of a hardware structure of an data processing apparatus of the embodiment.

Next, an example of a hardware structure of the data processing apparatus 20 is described with reference to FIG. 2. FIG. 2 is a block diagram illustrating an example of a hardware structure of the data processing apparatus 20. The data processing apparatus 20 includes an input device 31, an output device 32, a drive device 33, an auxiliary memory 34, a main memory 35, a CPU (Central Processing Unit) 36 and a communication control device 37. These are connected with each other by a system bus B.

The input device 31 includes an operation device such as a keyboard or a mouse, and accepts an instruction to perform a game, an instruction to activate a setting screen or various other inputs, in accordance with an operation by the user U to the operation device. The input device 31 may include the controller 40.

The output device 32 includes a display, and displays an image corresponding to a game progression or the setting screen. The HMD 10 is an example of the output device 32.

The auxiliary memory 34 is actualized by a HDD (Hard Disk Drive), an SSD (Solid State Drive) or the like, for example. The auxiliary memory 34 stores programs or data. The programs or data stored in the auxiliary memory 34 include a program that controls the entirety of the data processing apparatus 20, a program for executing predetermined application and the like.

The main memory 35 may be configured by a ROM (Read Only Memory) or a RAM (Random Access Memory). The CPU 36 may read out the programs or data from the auxiliary memory 34 to the main memory 35, and control the progression of the game by performing the game, or actualizes other functions of the data processing apparatus 20.

The communication control device 37 performs a radio communication with the HMD 10, or communicates with a server or other external devices via a network.

The data processing apparatus 20 is capable of reading out from and writing on a recording medium 38 via the drive device 33. The recording medium 38 may be a CD (Compact Disk), a DVD (Digital Versatile Disk), an SD Memory card, an USB (Universal Serial Bus) memory or the like.

(Functional Structure of Data Processing Apparatus)

Figure 3:
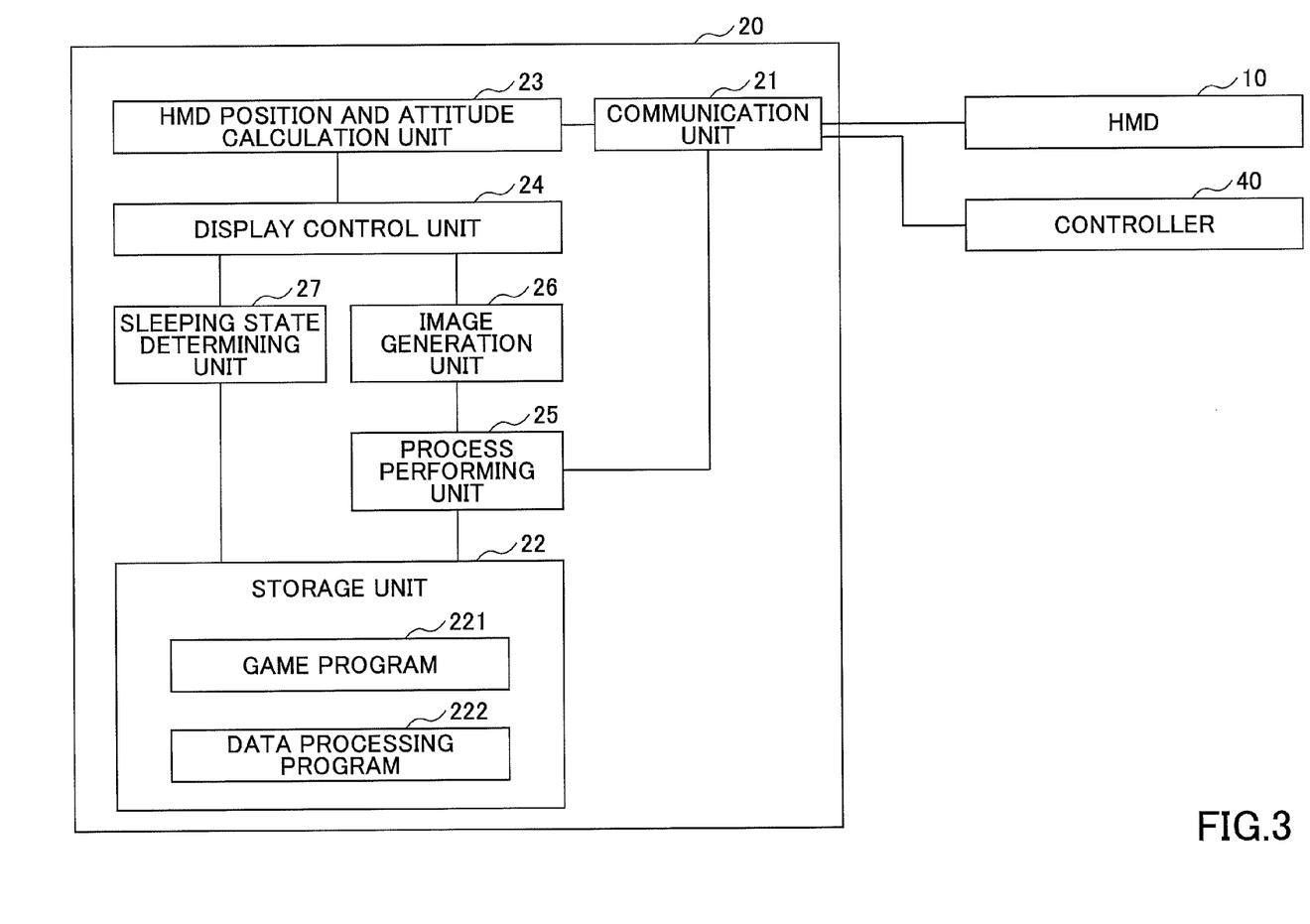
FIG. 3 is a view illustrating an example of a functional structure of the data processing apparatus of the embodiment.

Next, an example of a functional structure of the data processing apparatus 20 of the embodiment is described with reference to FIG. 3. FIG. 3 is a block diagram illustrating an example of a functional structure of the data processing apparatus 20.

The data processing apparatus 20 includes a communication unit 21, a storage unit 22, a HMD position and attitude calculation unit 23, a display control unit 24, a process performing unit 25, an image generation unit 26 and a sleeping state determining unit 27.

The communication unit 21 sends and receives data between the HMD 10 and the controller 40 that are connected via a network. Further, the communication unit 21 sends and receives various data that are used when downloading a game program from an external device.

The storage unit 22 stores a game program 221, a data processing program 222 and various data.

The HMD position and attitude calculation unit 23 tracks the HMD 10 using an image that is obtained by the color image sensor 12 and calculates a position and a direction (an angle) of a head, a face or a neck of the user U. The HMD position and attitude calculation unit 23 may track eyes of the user U using the image obtained by the color image sensor 12. Alternatively, the HMD position and attitude calculation unit 23 may track the eyes of the user U using an image obtained by a camera that is different from the color image sensor 12.

The image generation unit 26 generates a game image to be displayed on the HMD 10. The image generation unit 26 generates a game image that corresponds to the calculated position and direction of the head or the face of the user. The display control unit 24 displays the image generated by the image generation unit 26 in a virtual space of the HMD 10 in accordance with a game progression.

The process performing unit 25 performs a desired game. While the process performing unit 25 performs the game, in other words, while the user U is playing the game, the sleeping state determining unit 27 determines whether the user is in a sleeping state based on the calculated position or the direction of the head, the face or the neck of the user U. Specifically, the sleeping state determining unit 27 determines that the user is in the sleeping state when a candidate state, in which at least one of the calculated position and the direction of the head, the face or the neck of the user U is shifted greater than or equal to a predetermined set amount, continues for greater than or equal to a predetermined set period (a predetermined first set period, or a predetermined second set period). Furthermore specifically, first, the sleeping state determining unit 27 determines whether the user is in the candidate state. Then, when the user is in the candidate state, the sleeping state determining unit 27 determines whether the user is in the candidate state for greater than or equal to the predetermined set period. Then, when the user is in the candidate state for greater than or equal to the predetermined set period, the sleeping state determining unit 27 determines that the user is in the sleeping state.

Furthermore, after the user is determined to be in the sleeping state, the process performing unit 25 performs a predetermined sleeping countermeasure process. As an example of the sleeping countermeasure process, the process performing unit 25 temporarily suspends the game. Meanwhile, the sleeping state determining unit 27 determines whether the user is recovered from the sleeping state, for example, every predetermined period. When it is determined that the user is recovered from the sleeping state, the process performing unit 25 restarts the game.

FIG. 3 illustrates a block diagram of a functional structure of the data processing apparatus 20. The individual constituents of the data processing apparatus 20 may be embodied by arbitrary combinations of hardware and software, typified by a CPU of an arbitrary computer, a memory, a program loaded in the memory so as to embody the constituents illustrated in the drawings, a storage unit for storing the program such as a hard disk, and an interface for network connection. It may be understood by those skilled in the art that methods and devices for the embodiment allow various modifications.

With such a structure, in the data processing apparatus 20 of the embodiment, the CPU 36 executes a game process and a sleeping state determination process using the game program, the data processing program and the various data stored in the main memory 35 or the auxiliary memory 34.

(Virtual Reality Space)

The coordinate system of the position and the direction of the head or the like of the user U in the real space is measured based on the image obtained by the color image sensor 12. The virtual space displayed on the HMD 10 is defined by a coordinate system in which coordinate axes are set in accordance with a horizontal direction and a vertical direction of the real space, and in which a scale is also set similarly to the real space.

Figure 4:
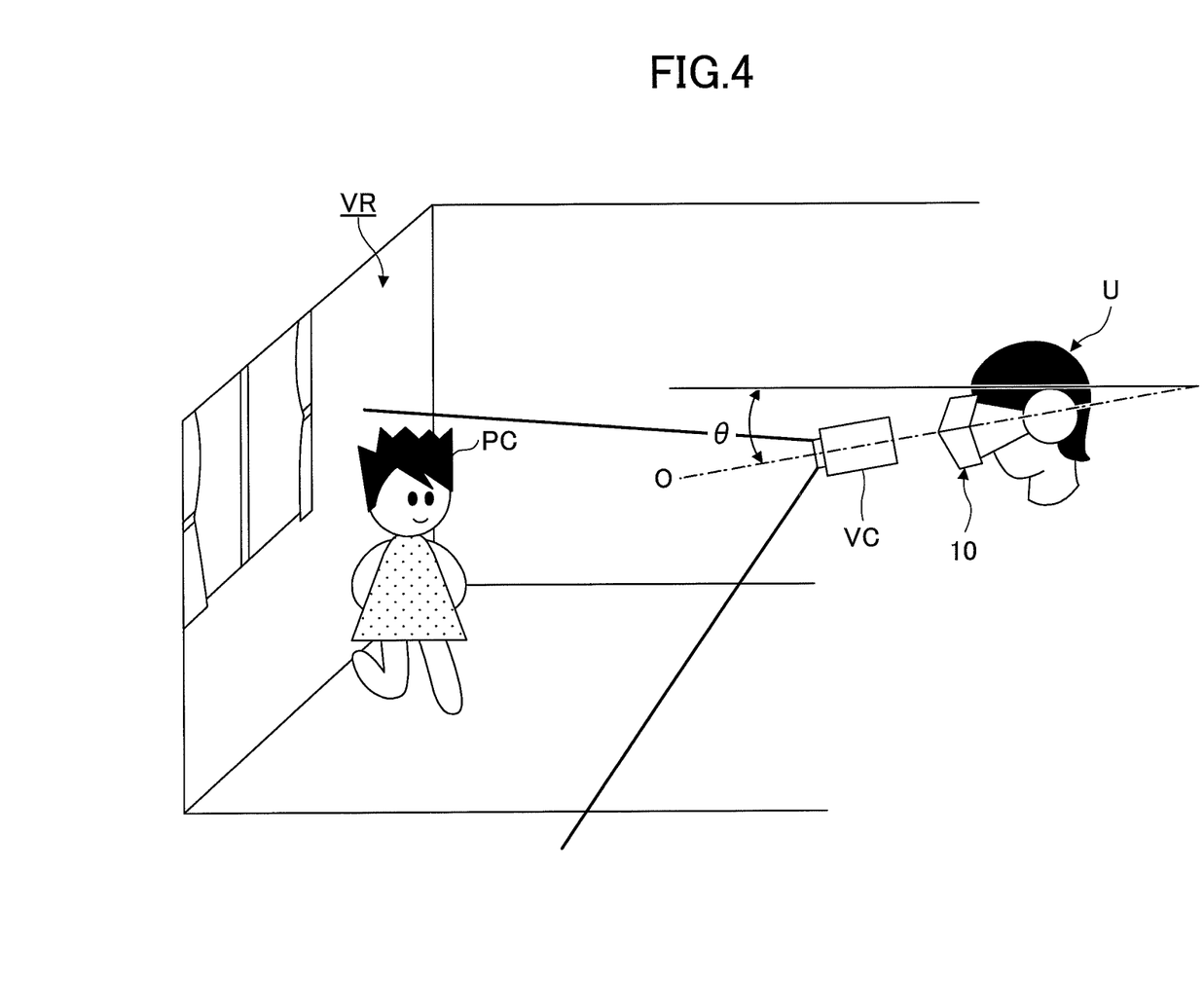
FIG. 4 is a view illustrating an example of a virtual camera for actualizing a virtual reality space of the embodiment.

FIG. 4 illustrates an example of a virtual reality space VR displayed by the HMD 10. The image displayed in the virtual reality space VR is obtained by a virtual camera VC. The virtual camera VC is provided at a position in the virtual space of the HMD 10, for which the coordinate is appropriately converted from the coordinate system of the real space to the coordinate system of the virtual space. A direction of an optical axis O of the virtual camera VC is controlled to a forward direction of the user U from the position of the head of the user U detected by the six-axis sensor 13 of the HMD 10. Further, the rotation of the virtual camera VC around the optical axis O is controlled to an angle θ for which the direction of the head of the user U rotates around the optical axis based on the attitude of the user U detected by the six-axis sensor 13. This means that when the position of the user U in the real space is moved, in accordance with this, the position of the virtual camera VC in the virtual space moves at a same scale. Further, when the head or the neck of the user in the real space is tilted in a predetermined direction, in accordance with this, the attitude of the virtual camera VC in the virtual space is tilted in the predetermined direction. As such, the virtual camera VC is controlled to trace the motion of the head, the face or the neck of the user U. For this function, a previously known head tracking technique of a HMD can be used.

First Embodiment (Starting of Game Process)

Figure 5:
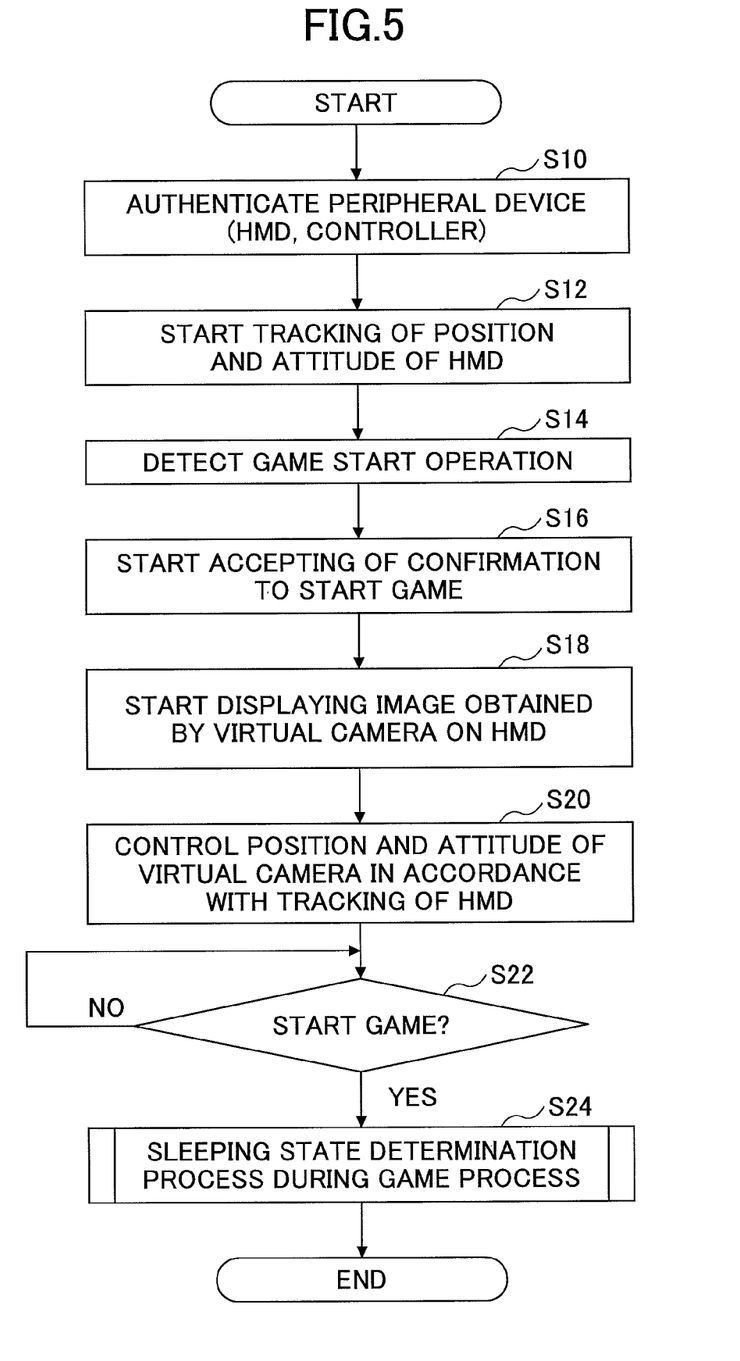
FIG. 5 is a flowchart illustrating an example of starting of a game process of the embodiment.

Next, starting of the game process of the first embodiment is described with reference to FIG. 5. FIG. 5 is a flowchart illustrating an example of starting of the game process of the first embodiment. The game process of the embodiment is actualized mainly by the process performing unit 25 to perform the game program 221.

When this process is started, the process performing unit 25 authenticates peripheral devices (the HMD 10 and the controller 40, for example) (step S10). When the device authentication is successfully finished, the communication unit 21 receives data of the image obtained by the color image sensor 12 every predetermined period. The HMD position and attitude calculation unit 23 starts tracking of the position and the attitude of the HMD 10 based on the data of the received images (step S12).

Next, when a predetermined operation of starting a game is input from the controller 40, the process performing unit 25 detects it (step S14), and starts accepting of a confirmation to start the game (step S16). The image generation unit 26 positions the virtual camera VC at an initial position in the virtual reality space VR, and generates an image of the virtual reality space VR obtained by the virtual camera VC. The display control unit 24 controls to display the generated image on the HMD 10 (step S18).

Next, the display control unit 24 controls the position and the attitude of the virtual camera VC in accordance with the tracking of the HMD 10 (step S20). Next, the process performing unit 25 determines whether to start the game (step S22). Upon accepting the confirmation to start the game from the controller 40 (from the user U), the process performing unit 25 determines to start the game. Then, the data processing apparatus 20 starts the game and performs the sleeping state determination process during the game process (step S24). This process is described later in detail with reference to FIG. 6. After performing the game process and the sleeping state determination process, the process is finished.

(Game Process and Sleeping State Determination Process in Game Process)

Figure 6:
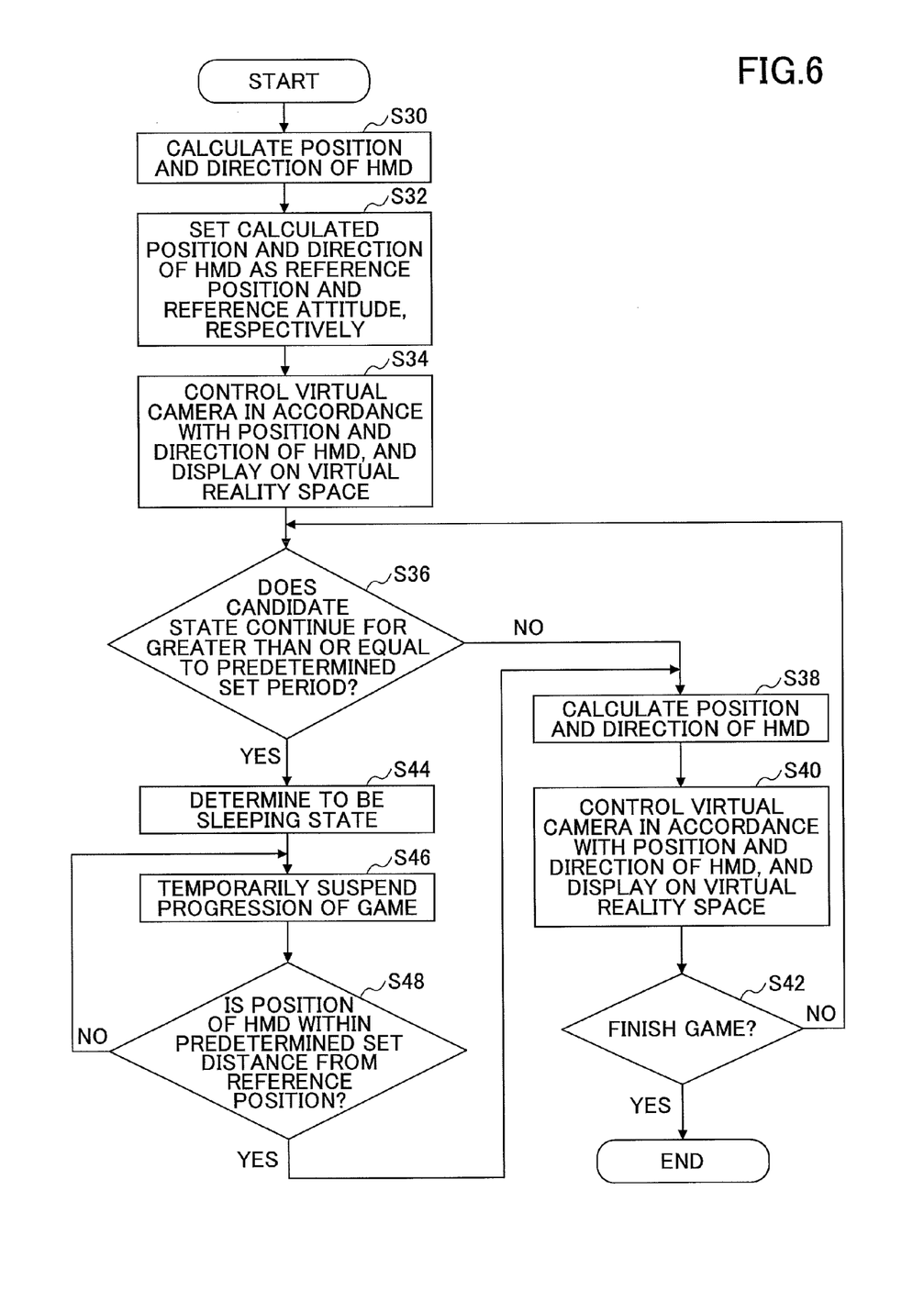
FIG. 6 is a flowchart illustrating an example of the game process and a sleep determination process in the game process of a first embodiment.

FIG. 6 is a flowchart illustrating an example of the game process and the sleeping state determination process of the first embodiment. The sleeping state determination process is performed while the game process is performed. The sleeping state determination process is actualized mainly by the sleeping state determining unit 27 to perform the data processing program 222.

As described in FIG. 5, the sleeping state determination process may be started when the game is started. When the sleeping state determination process is started, the HMD position and attitude calculation unit 23 calculates the position and the direction of the HMD 10 every predetermined period based on the image data received from the HMD 10 (step S30).

Next, the sleeping state determining unit 27 sets the calculated position of the HMD 10 as a reference position of the user U, and sets the calculated direction (angle) of the HMD 10 as a reference attitude of the user U (step S32). As it is assumed that the user U does not sleep at least when the game is started, the position and the direction of the head of the user U (in other words, the HMD 10) at the start of the game are set as the reference position and the reference attitude of the user U, respectively, when the user U is awake. The reference position or the reference attitude is used for a reference to determine whether the user U is in the sleeping state during the game. In the first embodiment, the sleeping state determining unit 27 may set only the calculated position of the HMD 10 as the reference position of the user U in step S32.

The image generation unit 26 controls the virtual camera VC in accordance with the position and the direction of the HMD 10, and generates the image obtained by the virtual camera VC. The display control unit 24 displays the generated image on the virtual reality space VR (step S34). This process is also a process of the game process.

Figure 7A:
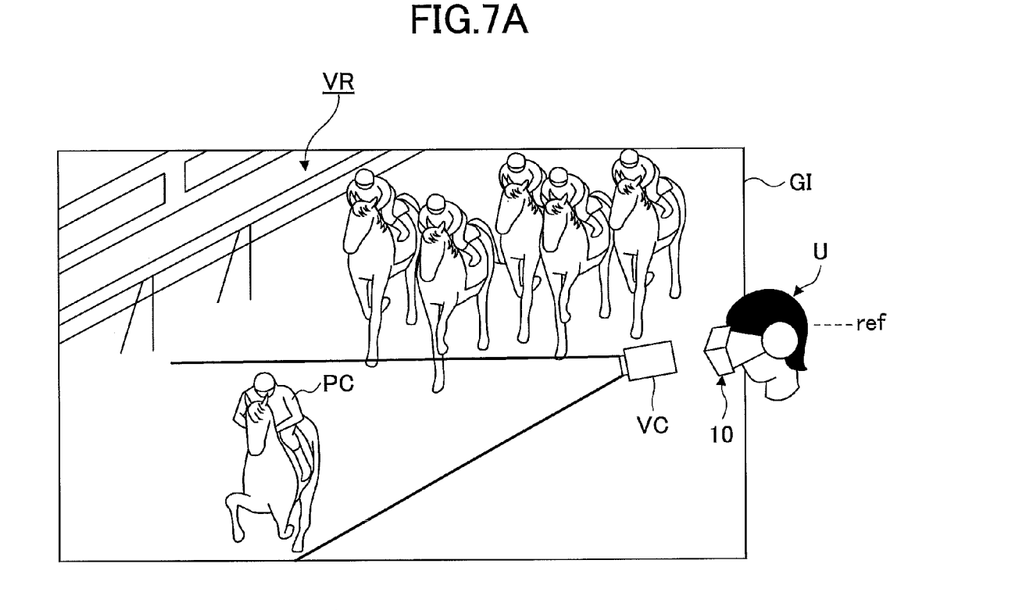
FIG. 7A and FIG. 7B are views illustrating an example of game images of the first embodiment.

FIG. 7A illustrates an example of the reference position "ref" of the user U who wears the HMD 10. At this time, a game image GI and the virtual camera VC have a relationship as schematically illustrated in FIG. 7A.

Figure 8A:
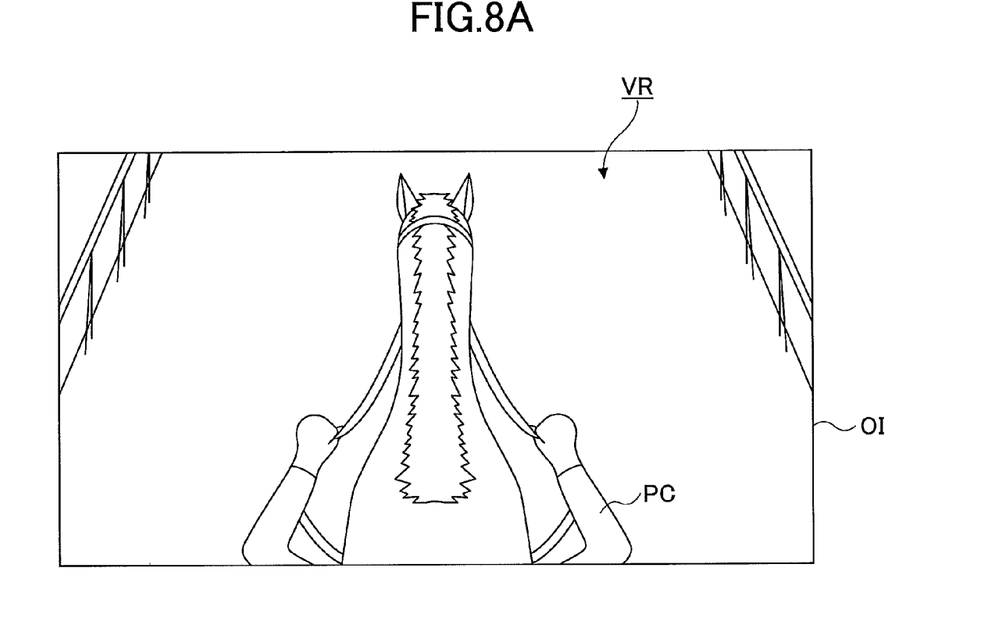
FIG. 8A and FIG. 8B are views illustrating an example of screens displayed on the HMD of the first embodiment.

FIG. 8A illustrates an image OI in the virtual reality space VR obtained by the virtual camera VC in accordance with the position and the direction of the user U as illustrated in FIG. 7A. At this time, the player character PC operated by the user U is positioned at height that the player character PC is riding on a horse. With this, the user U can unite with the player character PC of the game, and can be immersed in the game as if the user U is actually participating in a horse race in the virtual reality space VR. The position of the user U in FIG. 7A, and the position of the player character PC in 8A are at the reference position when the user U is awake, and FIG. 7A and FIG. 7A indicate a state when the user U is awake.

Next, the sleeping state determining unit 27 determines whether the user U is in the sleeping state. Specifically, first, the sleeping state determining unit 27 determines whether the user U is in the candidate state based on the position of the HMD 10. The sleeping state determining unit 27 determines that the user U is in the candidate state when the position of the HMD 10 is below the reference position by greater than or equal to a predetermined set distance. Then, when it is determined that the user U is in the candidate state, the sleeping state determining unit 27 determines whether the candidate state continues for greater than or equal to the predetermined set period (first set period) (step S36).

For example, when the position of the user U is as illustrated in FIG. 7A, this means that the user U is within the predetermined set range from the reference position "ref". Thus, referring back to step S36 of FIG. 6, the sleeping state determining unit 27 determines that the user U is not in the candidate state, in other words, that the position of the HMD 10 (in other words, the calculated position of the head of the user U) is not below the reference position by greater than or equal to the predetermined set distance (NO of step S36). Then, the process proceeds to step S38. Similar to step S30, the HMD position and attitude calculation unit 23 calculates the position and the direction of the HMD 10 based on the image data received from the HMD 10 (step S38). Then, similar to step S34, the image generation unit 26 controls the virtual camera VC in accordance with the position and the direction of the HMD 10, and generates an image obtained by the virtual camera VC. The display control unit 24 displays the generated image on the virtual reality space VR (step S40). Next, the process performing unit 25 determines whether to finish the game (step S42). When the process performing unit 25 determines not to finish the game (NO of step S42), the process returns to step S36, and the processes from step S36 are repeated. On the other hand, when the process performing unit 25 determines to finish the game (YES of step S42), the process is finished.

Figure 7B:
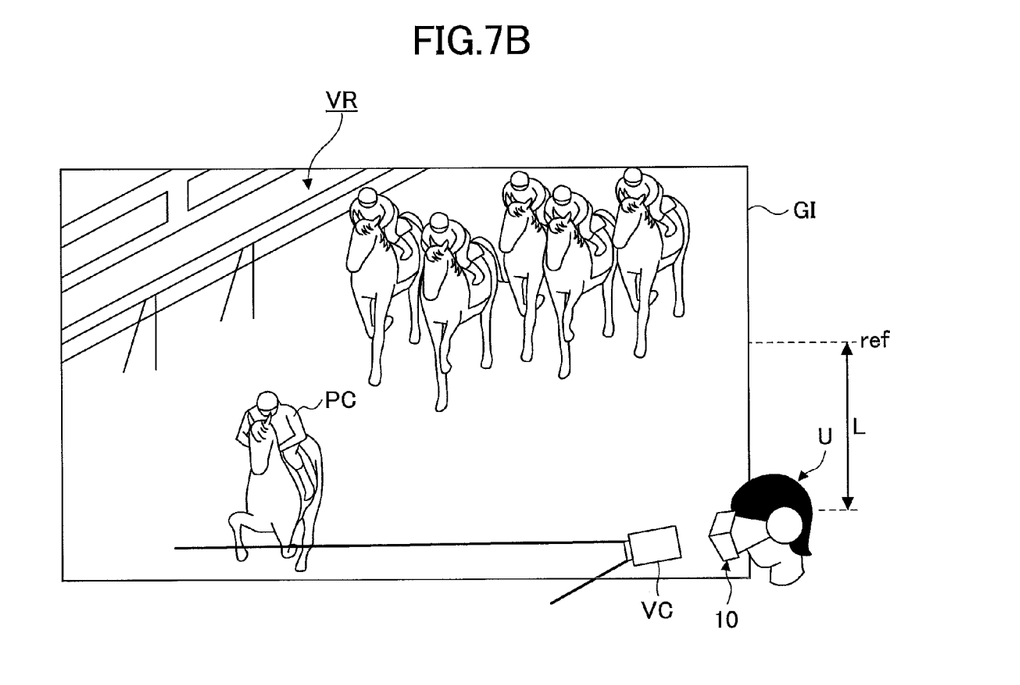

On the other hand, FIG. 7B illustrates an example a position of the user U who wears the HMD 10, that is shifted from the reference position "ref" by a distance "L". Here, it is assumed that the distance "L" is below the reference position "ref" by greater than the predetermined set distance. At this time, the game image GI and the virtual camera VC have a relationship as schematically illustrated in FIG. 7B.

Figure 8B:
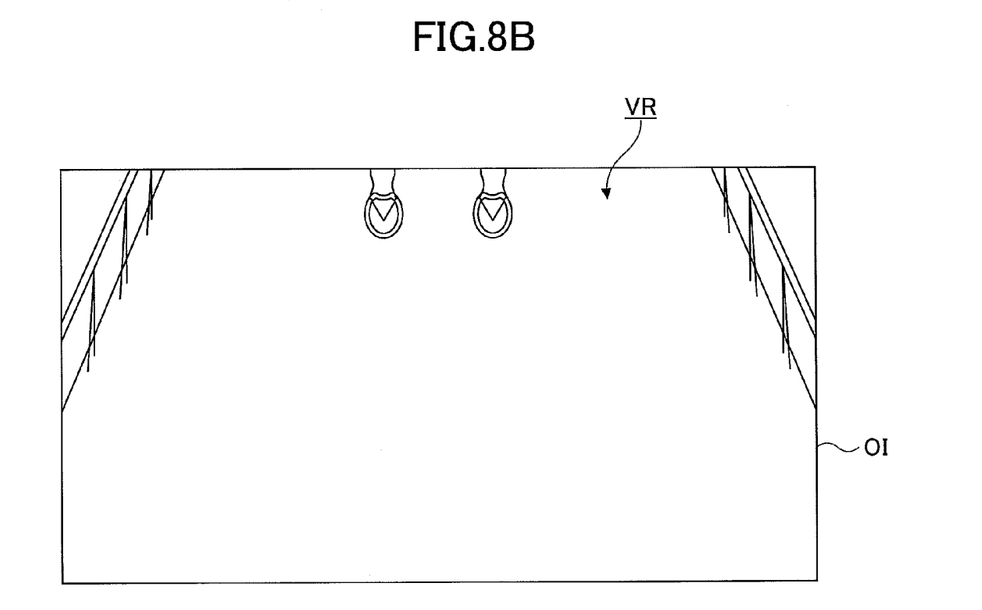

FIG. 8B illustrates the image OI in the virtual reality space VR obtained by the virtual camera VC in accordance with the position and the direction of the user U as illustrated in FIG. 7B. At this time, the player character PC operated by the user U is positioned at height near the ground, not the height that the player character PC is riding on the horse.

Thus, referring back to step S36 of FIG. 6, at this time, the sleeping state determining unit 27 determines that the user U is in the candidate state, in other words, that the position of the HMD 10 (in other words, the calculated position of the head of the user) is below the reference position by greater than or equal to the predetermined set distance. Then, subsequently, the sleeping state determining unit 27 determines whether this candidate state continues for greater than or equal to the predetermined set period (step S36).

When the sleeping state determining unit 27 determines that the candidate state does not continue for greater than or equal to the predetermined set period (NO of step S36), the process proceeds to step S38.

On the other hand, when the sleeping state determining unit 27 determines that the candidate state continues for greater than or equal to the predetermined set period (YES of step S36), the sleeping state determining unit 27 determines that the user U is in the sleeping state (S44). Then, the process performing unit 25 temporarily suspends the progression of the game (step S46). After temporarily suspending the progression of the game, the sleeping state determining unit 27 determines whether the position of the HMD 10 is within the predetermined set distance from the reference position, for example, every predetermined period (step S48). The process performing unit 25 terminates the progression of the while it is determined that the position of the HMD 10 is below the reference position by greater than or equal to the predetermined set distance (NO of step S48, and step S46). Then, the process performing unit 25 proceeds to step S38 when it is determined that the position of the HMD 10 is within the predetermined set distance from the reference position (YES of step S48), and restarts the game by performing the processes from step S38.

According to the above described game process and the sleeping state determination process of the first embodiment, the HMD 10 is tracked and the position and the direction of the head of the user U are calculated. Then, the image OI (see FIG. 8A or FIG. 8B) of the game process is displayed in the virtual reality space VR in accordance with the position of the HMD 10 (that is the calculated position of the head of the user U). Then, whether the candidate state, in which the calculated position of the head of the user U is shifted by greater than or equal to the predetermined set distance, continues for greater than or equal to the predetermined set period is determined. Then, when it is determined that the candidate state continues for greater than or equal to the predetermined set period, the user U is determined to be in the sleeping state. Then, progression of the game is temporarily suspended, and when the user U wakes up, the progression of the game is restarted. With this configuration, the sleeping state of the user U who wears the HMD 10 can be accurately determined.

Second Embodiment (Game Process and Sleeping State Determination Process in Game Process)

Next, the game process and the sleeping state determination process of the second embodiment are described with reference to FIG. 9. As starting of the game process of the second embodiment is the same as that of the first embodiment of FIG. 5, the description is not repeated.

Figure 9:
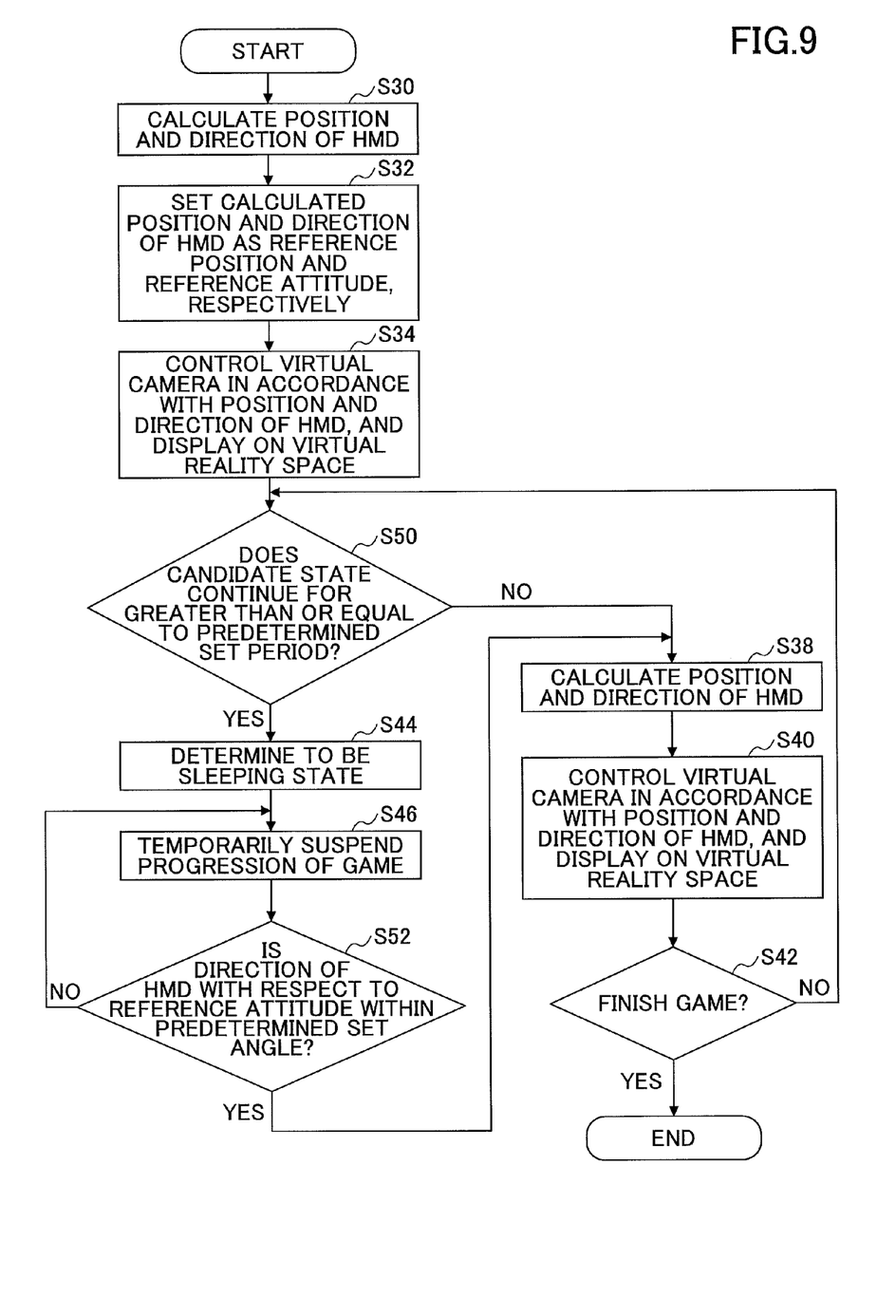
FIG. 9 is a flowchart illustrating an example of the game process and the sleep determination process in the game process of a second embodiment.

The sleeping state determination process of the second embodiment of FIG. 9 is different from the sleeping state determination process of the first embodiment of FIG. 6 in that step S36 of FIG. 6 is changed to step S50, and step S48 of FIG. 6 is changed to step S52. As the remaining steps are the same, only the processes of step S50 and step S52 that are different from the first embodiment are described.

Here, in the second embodiment, the sleeping state determining unit 27 may set only the calculated direction of the HMD 10 as the reference attitude of the user U in step S32.

In step S50, the sleeping state determining unit 27 determines whether the user U is in the sleeping state. Specifically, first, the sleeping state determining unit 27 determines whether the user U is in the candidate state based on the direction of the HMD 10. The sleeping state determining unit 27 determines that the user U is in the candidate state when the direction of the HMD 10 directs below by greater than or equal to a predetermined set angle from the reference attitude. Then, when it is determined that the user U is in the candidate state, the sleeping state determining unit 27 determines whether the candidate state continues for greater than or equal to a predetermined set period (second set period).

Figure 10A:
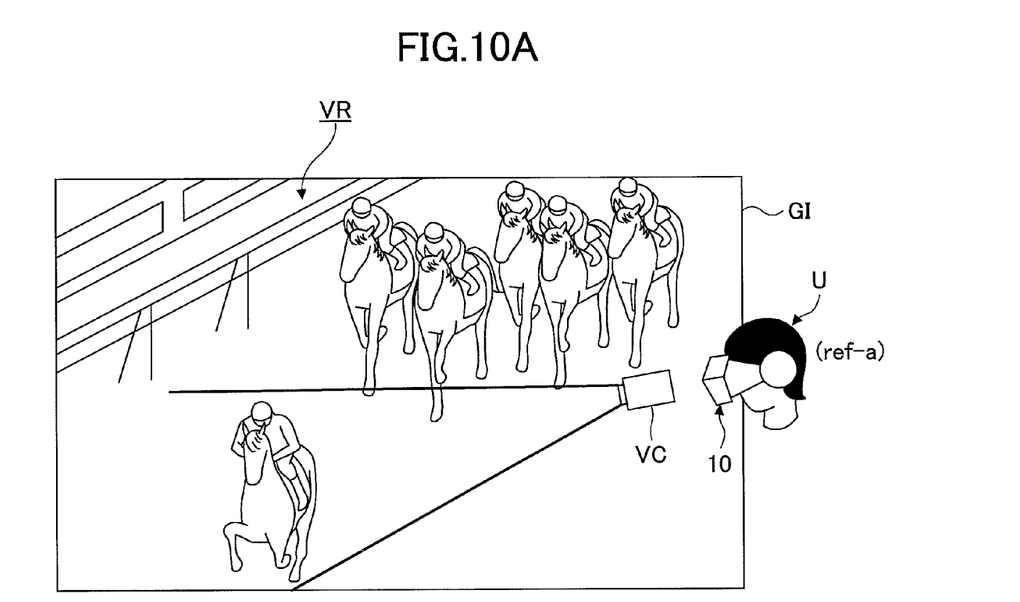
FIG. 10A and FIG. 10B are views illustrating an example of screens displayed on the HMD of the second embodiment.

FIG. 10A illustrates an example of the reference attitude "ref-a" of the user U who wears the HMD 10. At this time, the game image GI and the virtual camera VC have a relationship as schematically illustrated in FIG. 10A. At this time, the image OI in the virtual reality space VR obtained by the virtual camera VC in accordance with the position and the direction of the user U as illustrated in FIG. 10A becomes as illustrated in FIG. 8A. This means that the direction of the player character PC in 8A are at the reference position when the user U is within the predetermined set range from the reference attitude "ref-a".

In such a case, referring back to FIG. 9, the sleeping state determining unit 27 determines that the user U is not in the candidate state, in other words, that the direction of the HMD 10 (in other words, the calculated direction of the head of the user U) does not direct below by greater than or equal to the predetermined set angle from the reference attitude (NO of step S50). Then, the process proceeds to step S38 and the processes from step S38 are performed.

Figure 10B:
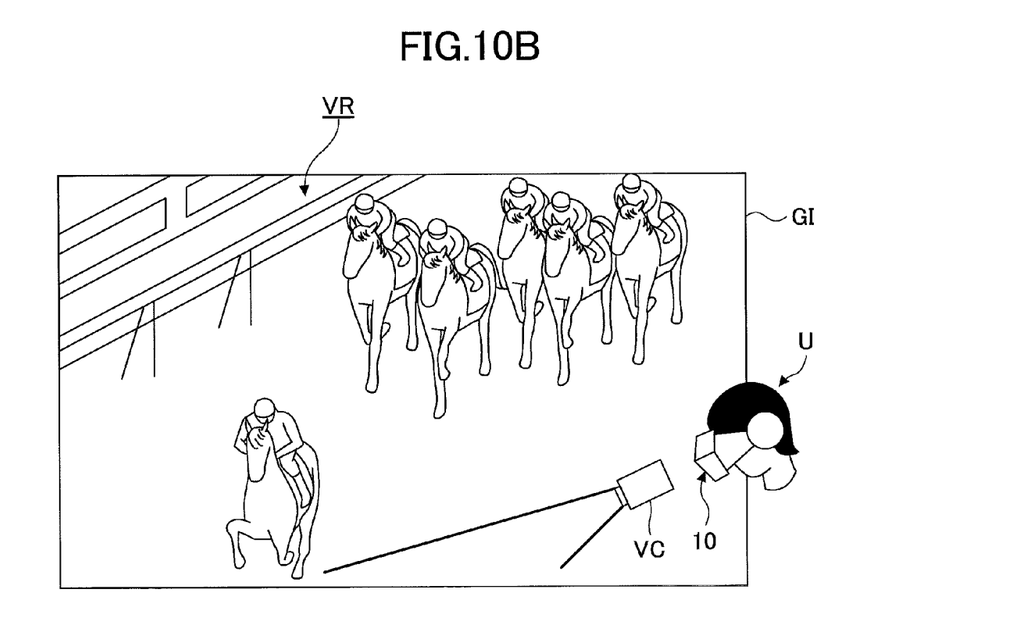

On the other hand, FIG. 10B illustrates an example an attitude of the user U who wears the HMD 10, that is shifted from the reference attitude "ref-a" by an angle which is assumed to direct below by greater than the predetermined set angle from the reference attitude. At this time, the game image GI and the virtual camera VC have a relationship as schematically illustrated in FIG. 10B. Then, the image OI obtained by the virtual camera VC in accordance with the position and the direction of the user U becomes as illustrated in FIG. 8B.

Thus, referring back to step S50 of FIG. 9, at this time, the sleeping state determining unit 27 determines that the user U is in the candidate state, in other words, that the direction of the HMD 10 (in other words, the calculated direction of the head of the user) directs below by greater than or equal to the predetermined set angle from the reference attitude. Then, subsequently, the sleeping state determining unit 27 determines whether this candidate state continues for greater than or equal to the predetermined set period (step S50).

When the sleeping state determining unit 27 determines that the candidate state does not continue for greater than or equal to the predetermined set period (NO of step S50), the process proceeds to step S38.

On the other hand, when the sleeping state determining unit 27 determines that the candidate state continues for greater than or equal to the predetermined set period (YES of step S50), the sleeping state determining unit 27 determines that the user U is in the sleeping state (step S44). As a result, the process performing unit 25 temporarily suspends the progression of the game (step S46).

Thereafter, the sleeping state determining unit 27 determines whether the direction of the HMD 10 is within the predetermined set angle from the reference attitude (step S52). When it is determined that the direction of the HMD 10 is within the predetermined set angle (YES of step S52), the HMD position and attitude calculation unit 23 performs the processes from step S38, and restarts the game.

According to the above described game process and the sleeping state determination process of the second embodiment, the HMD 10 is tracked and the position and direction of the head of the user U are calculated. Then, the image OI (see FIG. 8A or FIG. 8B) of the game process is displayed in the virtual reality space VR in accordance with the direction of the HMD 10 (that is the calculated direction of the head of the user U). Then, whether the candidate state, in which the calculated direction of the head of the user U directs below by greater than or equal to the predetermined set angle, continues for greater than or equal to the predetermined set period is determined. Then, when it is determined that the candidate state continues for greater than or equal to the predetermined set period, the user U is determined to be in the sleeping state. Then, when it is determined that the user U is in the sleeping state, the progression of the game is temporarily suspended. Further, when the user U wakes up, the progression of the game is restarted. With this configuration, similar to the first embodiment, the sleeping state of the user U who wears the HMD 10 can be accurately determined using the virtual reality technology.

Third Embodiment (Game Process and Sleeping State Determination Process in Game Process)

Next, the game process and the sleeping state determination process of the third embodiment are described with reference to FIG. 11. As starting of the game process of the third embodiment is the same as that of the first embodiment of FIG. 5, the description is not repeated.

Figure 11:
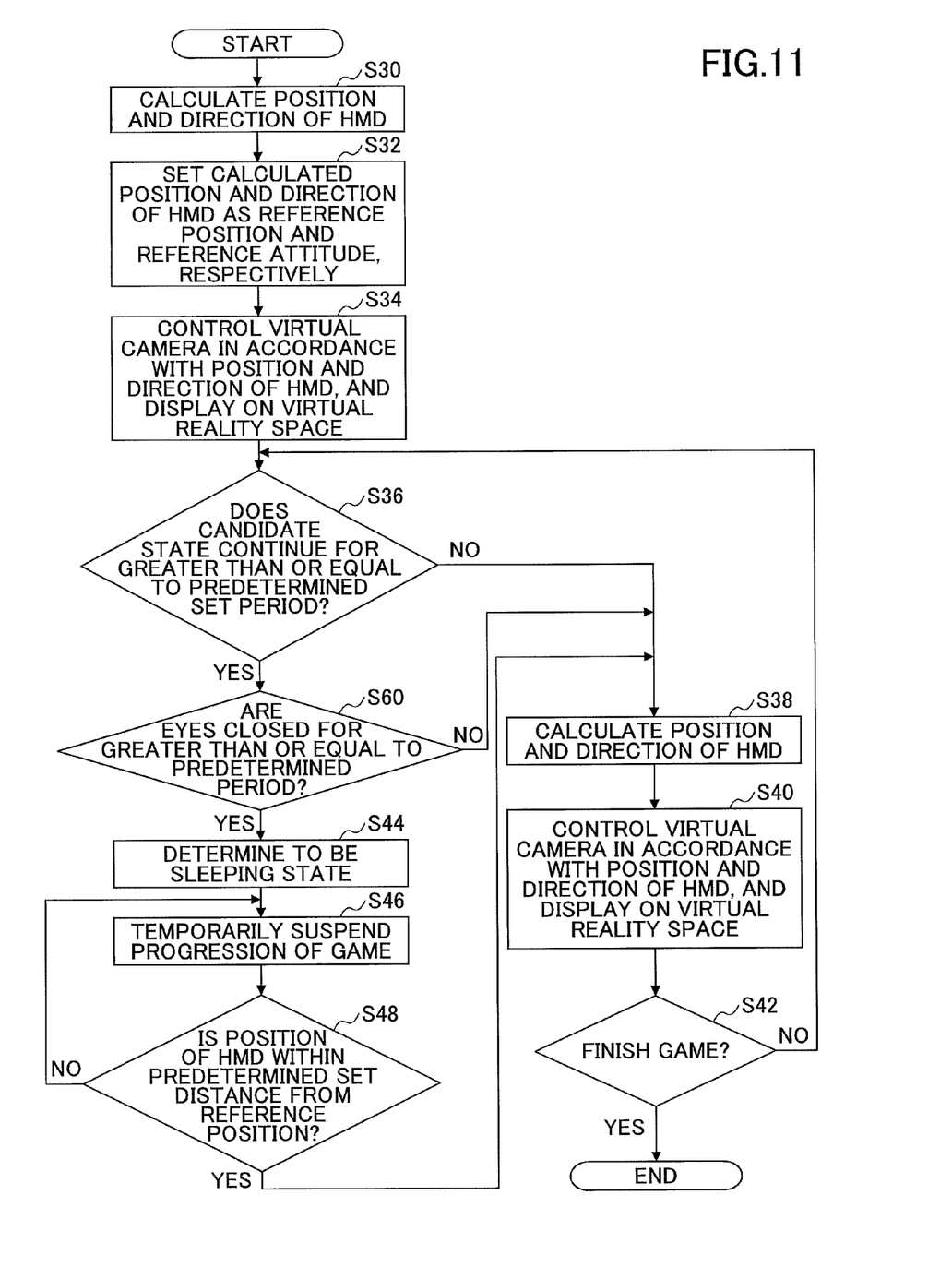
FIG. 11 is a flowchart illustrating an example of the sleep determination process in the game process of a third embodiment.

The sleeping state determination process of the third embodiment of FIG. 11 is different from the sleeping state determination process of the first embodiment of FIG. 6 in that step S60 is added, and the rest of the steps are the same. Thus, processes related to step S60 are described.

When the sleeping state determining unit 27 determines that the candidate state continues for greater than or equal to the predetermined set period (YES of step S36), the sleeping state determining unit 27 further determines whether eyes of the user U is closed for greater than or equal to a predetermined set period (a predetermined third set period) (step S60). When it is determined that the eyes of the user U are open (NO of step S60), the sleeping state determining unit 27 determines that the user U is not sleeping and proceeds to step S38. Then, the processes from step S38 are performed.

On the other hand, when it is determined that the eyes of the user U are closed for greater than or equal to the predetermined set period (YES of step S60), the sleeping state determining unit 27 determines that the user U is in the sleeping state (step S44), and temporarily suspends the progression of the game (step S46). Even though when it is determined that the eyes of the user U are closed, the period in which the user closes his/her eyes does not continue for greater than or equal to the predetermined set period (NO of step S60), the sleeping state determining unit 27 determines that the user U is not sleeping and proceeds to step S38.

According to the above described game process and the sleeping state determination process of the third embodiment, the HMD 10 and the eyes of the user U are tracked. Then, similar to the first and second embodiments, the image OI (see FIG. 8A or FIG. 8B) of the game process is displayed in the virtual reality space VR in accordance with the direction of the HMD 10 (that is the calculated direction of the head of the user U). whether the candidate state, in which the calculated position of the head of the user U is shifted by greater than or equal to the predetermined set distance, continues for greater than or equal to the predetermined set period (predetermined first set period) is determined. Then, when it is determined that the candidate state continues for greater than or equal to the predetermined set period, whether the user U closes his/her eyes for greater than or equal to the predetermined set period (predetermined third set period) is determined. Then, when it is determined that the user U closes his/her eyes for greater than or equal to the predetermined set period, the user U is determined to be in the sleeping state. According to the third embodiment, the sleeping state of the user U who wears the HMD 10 can be determined furthermore accurately based on the tracking result of the head and the tracking result of the eyes.

Here, instead of steps S36 and S48, steps S50 and S52 of the second embodiment may be performed.

Alternative Examples

The sleeping state determination process performed in the game process of each of the embodiments is described above. In the sleeping state determination process of each of the first to third embodiments, the motions of the virtual camera VC in the virtual space and the color image sensor 12 in the real space are matched to form the virtual reality space VR in the HMD 10. In each of the embodiments, by assuming the motion of the head of the image obtained by the color image sensor 12 as the motion of the HMD 10, and matching the motions of the virtual camera VC and the HMD 10, the user U can play the game as if the user U is actually in the virtual space.

Although it is assumed that the motion of the head of the user U is mainly assumed as the motion of the HMD 10, this is not limited so. For example, the virtual reality space VR may be actualized by assuming the motion of the face of the user U as the motion of the HMD 10, and matching the motions of the virtual camera VC and the HMD 10. Further, the virtual reality space VR may be actualized by assuming the motion of the neck of the user U as the motion of the HMD 10, and matching the motions of the virtual camera VC and the HMD 10.

According to the data processing apparatus 20 of the embodiment that actualizes the above described virtual reality space VR, the position and the attitude of the player character PC in the virtual space are set to be the same or is approximated to the position and the attitude of the user U who operates the game.

By using this principle, according to the sleeping state determination process of the first embodiment, whether the user U is in the sleeping state is determined by calculating the position of the HMD 10 (position of the head of the user U) based on head tracking, and comparing with the reference position, that is the position when the user U is awake.

Similarly, according to the sleeping state determination process of the second embodiment, whether the user U is in the sleeping state is determined by calculating the direction of the HMD 10 based on head tracking, and comparing with the reference attitude, that is the attitude when the user U is awake.

Similarly, according to the sleeping state determination process of the third embodiment, whether the user U is in the sleeping state is determined by using both the determination of the sleeping state based on the position of the HMD 10 of the first embodiment, and the determination based on open and close of the eyes of the user U.

However, the sleeping state determination process is not limited so, and the sleeping state of the user U may be determined based on both of the position of the HMD 10 and the attitude of the HMD 10, for example. Further, the sleeping state of the user U may be determined based on the attitude of the HMD 10 and open and close of the eyes of the user U. Further, the sleeping state of the user U may be determined based on all of the position of the HMD 10, the attitude of the HMD 10 and open and close of the eyes of the user U.

Further, when the user U is determined to be in the sleeping state, the progression of the game was temporarily suspended, as the predetermined sleeping countermeasure process, in the sleeping state determination process of each of the first to third embodiments. However, the predetermined sleeping countermeasure process that is performed when the user U is determined to be in the sleeping state is not limited so.

For example, when the user U is determined to be in the sleeping state, a content of the game may be automatically saved and the power of the HMD 10 may be switched off. With this, the user can restart the game from the state that is right before becoming the sleeping state.

Further, when the user U is determined to be in the sleeping state, alarming sound may be output from a speaker or the like provided at the HMD 10, or a character in the game may be caused to shout or the like, to wake the user U.

Further, when the user U is determined to be in the sleeping state, the player character PC operated by the operation of the user U may be switched to a non-player character NPC that is automatically operated by the data processing apparatus 20. In such a case, when the user U wakes up, the game can be continued without suspending by switching the non-player character NPC to the player character PC again. In particular, when the user U is playing a multiplayer game such as a communication game in which a plurality of users U plays the same game while communicating with each other, if one of the users U becomes in the sleeping state, the entire progression of the game may be interrupted. However, with the above sleeping countermeasure process, such an interruption can be prevented. Further, when the user U is determined to be in the sleeping state while the user U is playing the multiplayer game, notification that the user U is in the sleeping state may be sent to other users U.

Here, the predetermined set distance for determining that the user U is in the sleeping state (step S36) may be previously set as a value greater than or equal to 50 cm, based on a difference of positions between an awakening state (when the user U sits, for example) and a sleeping state (when the user U is lying down, for example) of the user U who has a standard size and form.

Further, the predetermined set angle for determining that the user U is in the sleeping state (step S50) may be previously set as a value greater than or equal to 30°, based on a difference of angles of the head, the face, the neck or the like of the user U who has a standard size and form between the awakening state (when the user U sits, for example), and the sleeping state (when the user U is lying down, for example).

Further, the predetermined set period for determining that the user U is in the sleeping state (steps S36, S50 and S60) is set to be a period greater than or equal to a period for which the user closes his/her eyes when the user have tired eyes or the like. For example, the predetermined period for determining that the user U is in the sleeping state may be about a minute to five minutes. Furthermore, the predetermined set period in steps S36, S50 and S60 may be the same, or may be different from each other.

Further, the sleeping state determination process of the first to third embodiments may not be limited to be performed in the game process. The sleeping state determination process may be performed at any time when ah image is displayed by the body-mounted display device such as when playing back screen images of a program or a movie, or the like.

According to the embodiments, a sleeping state of a user who wears a body-mounted display device can be accurately determined, by using a virtual reality technique.

Although a preferred embodiment of the non-transitory computer-readable recording medium and the data processing apparatus 20 has been specifically illustrated and described, it is to be understood that minor modifications may be made therein without departing from the spirit and scope of the invention as defined by the claims.

The present invention is not limited to the specifically disclosed embodiments, and numerous variations and modifications may be made without departing from the spirit and scope of the present invention.

What is claimed is:

1. A non-transitory computer-readable recording medium having recorded thereon a data processing program that causes a computer to execute a method to display an image of a predetermined process on a body-mounted display device worn by a user, the method comprising:

tracking a head, a face or a neck of the user, and calculating the position and the direction of the head, the face or the neck of the user;

displaying the image of the predetermined process in a virtual space of the display device such that a position and a direction of the predetermined image corresponds to the calculated position and direction of the head, the face or the neck of the user;

determining that the user is in the sleeping state when a candidate state, in which at least either of the calculated position and direction of the head, the face or the neck of the user is shifted by greater than or equal to a predetermined set amount, continues for greater than or equal to a predetermined set period; and performing a predetermined sleeping countermeasure process when it is determined that the user is in the sleeping state.

2. The non-transitory computer-readable recording medium according to claim 1, wherein the candidate state is that the calculated position of the head, the face or the neck of the user is below a set reference position by greater than or equal to a predetermined set distance.

3. The non-transitory computer-readable recording medium according to claim 1, wherein the candidate state is that the calculated direction of the head, the face or the neck of the user directs below with respect to a set reference attitude by greater than or equal to a predetermined set angle.

4. The non-transitory computer-readable recording medium according to claim 1, wherein the predetermined sleeping countermeasure process is at least one of (a) storing information indicating a content of a process performed by the user regarding the predetermined process in a storage unit, (b) finishing the predetermined process, (c) switching off a power source of the display device, (d) alarming the user that the user is in the sleeping state, (e) temporarily suspending the predetermined process, (f) switching control by the user to an automatic control for the process performed by the user regarding the predetermined process, and (g) notifying that the user is in the sleeping state to other users.

5. The non-transitory computer-readable recording medium according to claim 1, wherein in the determining that the user is in the sleeping state, the user is determined to in the sleeping state when the candidate state continues for greater than or equal to the predetermined set period and also a state in which the user closes its eyes for greater than or equal to another predetermined set period.

6. A data processing apparatus that controls to display an image of a predetermined process on a body-mounted display device worn by a user, comprising:

a position and attitude calculation unit that tracks a head, a face or a neck of the user, and calculates the position and the direction of the head, the face or the neck of the user;

a display control unit that displays the image of the predetermined process in a virtual space of the display device such that a position and a direction of the predetermined image corresponds to the calculated position and direction of the head, the face or the neck of the user;

a determining unit that determines that the user is in the sleeping state when a candidate state, in which at least either of the calculated position and direction of the head, the face or the neck of the user is shifted by greater than or equal to a predetermined set amount, continues for greater than or equal to a predetermined set period; and a process performing unit that performs a predetermined sleeping countermeasure process when it is determined that the user is in the sleeping state.

\* \* \* \* \*